United States Patent [19]

Pasternack

[11] Patent Number: 5,005,569

[45] Date of Patent: Apr. 9, 1991

[54] VENTILATORY AIR HUMIDIFIER FOR A BREATHING EQUIPMENT

[75] Inventor: Adalbert Pasternack, Bad Schwartau, Fed. Rep. of Germany

[73] Assignee: Drägerwerk Aktiengesellschaft, Lübeck, Fed. Rep. of Germany

[21] Appl. No.: 350,846

[22] Filed: May 11, 1989

[30] Foreign Application Priority Data

Jun. 11, 1988 [DE] Fed. Rep. of Germany ....... 3819988

[51] Int. Cl.[5] ............................................ A61M 15/00

[52] U.S. Cl. ........................... 128/204.13; 128/203.12

[58] Field of Search ...................... 128/200.24, 203.12, 128/204.18, 200.11, 200.13, 203.16, 204.13, 204.14, 207.14, 911

[56] References Cited

U.S. PATENT DOCUMENTS

| | | | |
|---|---|---|---|
| 4,146,597 | 3/1979 | Eckstein et al. | 128/204.13 |
| 4,155,961 | 5/1979 | Benthin | 128/204.13 |
| 4,318,398 | 3/1982 | Oetjen et al. | 128/204.13 |
| 4,327,717 | 5/1982 | Oetjen et al. | 128/204.13 |
| 4,355,636 | 10/1982 | Oetjen et al. | 128/204.13 |
| 4,367,734 | 1/1983 | Benthin | 128/204.13 |
| 4,381,267 | 4/1983 | Jackson | 128/204.13 |

FOREIGN PATENT DOCUMENTS

| | | | |
|---|---|---|---|
| 1090704 | 5/1986 | Japan | 128/200.24 |
| 2225206 | 10/1987 | Japan | 128/200.24 |

*Primary Examiner*—Edgar S. Burr

*Assistant Examiner*—Kimberly L. Asher

*Attorney, Agent, or Firm*—McGlew and Tuttle

[57] ABSTRACT

An air venting humidifer for breathing equipment which is installed in the duct draft of a ventilation air tube between a ventilation air source and a ventilation air connection piece comprises a multi-layered water-impermeable but steam permeable membrane. The membrane has a separation wall which is surrounded by a water-filled humidification chamber having a flexible outer wall. Pressure can be exerted on this outer wall by air pressure in a surrounding ventilation air chamber containing and conveying the ventilation air. The humidification output of the air becomes independent of the pressure in the interior of the hollow fiber air flow chambers and the humidification of the ventilation air is adjusted to the requirements of the user. For this purpose the outer wall of the humidification chamber is surrounded by an antechamber which can be filled with the ventilation air and which is connected with the ventilation air chamber by means of a throttle.

8 Claims, 1 Drawing Sheet

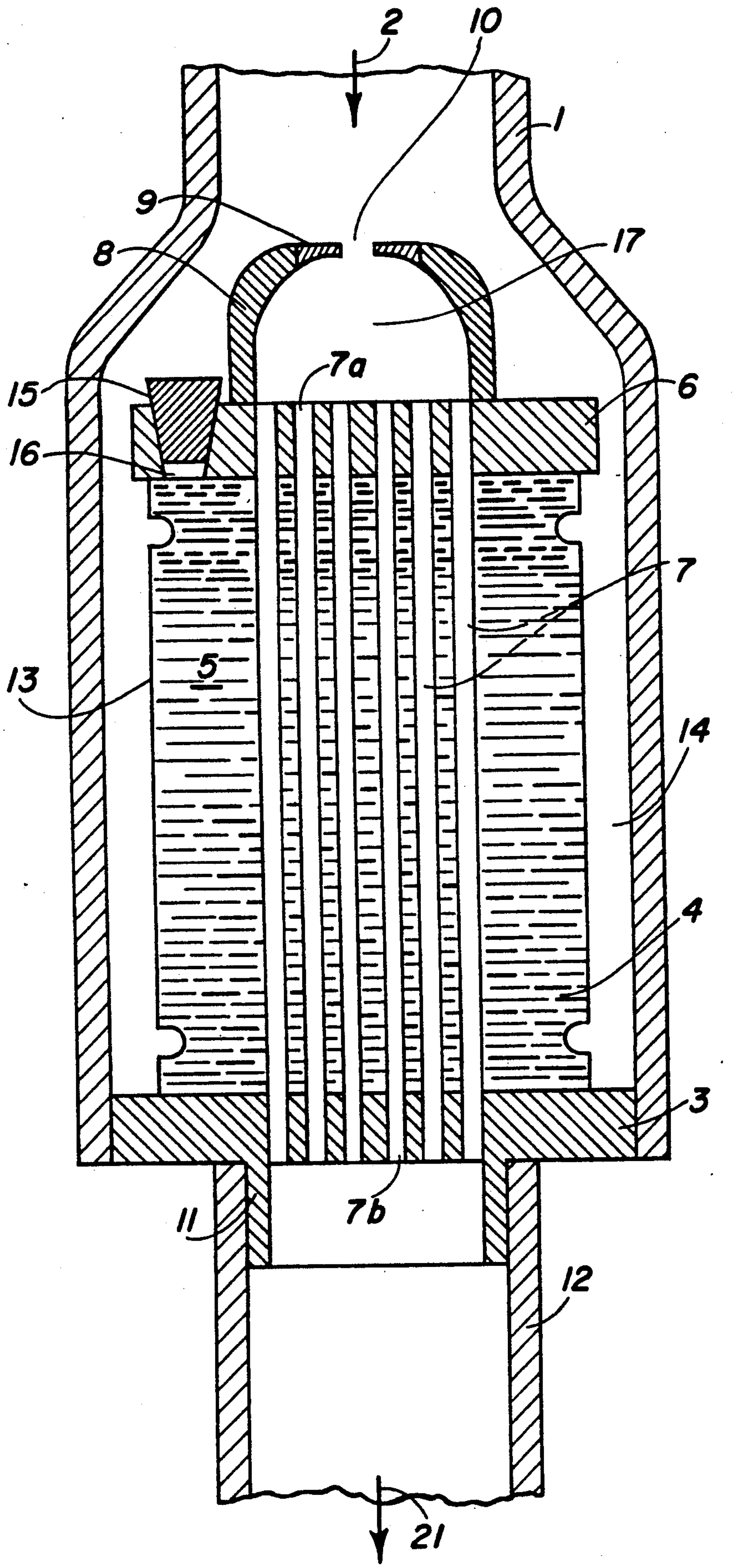
2
10
1
9
8
17
7a
15
6
16
7
13
5
14
4
3
11
7b
12
21

VENTILATORY AIR HUMIDIFIER FOR A BREATHING EQUIPMENT

FIELD AND BACKGROUND OF THE INVENTION

The present invention relates in general to breathing equipment and in particular to a new and useful ventable air humidifier for breathing equipment.

A similar ventilation air humidifier is known from German Patent DE-AS 29 00 484. A known ventilation air humidifier has a multilayered vaporization separation membrane in the shape of a hollow fiber bundle. The ventilation air can flow through the single hollow fiber. Each hollow fiber is surrounded by water as the humidifying liquid, which is held in a humidifying chamber whose flexible outer surface is biased by a pressure spring. Due to the pressure generated, an increased amount of steam is pressed in the ventilation air chamber through the semipermeable membrane so that the inhaled ventilation air is enriched with steam.

In the known ventilation air humidifier it is a disadvantage that the degree of humidification depends on the pressure in the ventilation air tube which again is a function of the breathing of the user. If, in the known ventilation air humidifier, the air path pressure increases in the interior of the hollow fiber, the pressure exerted on the humidifying chamber by means of the force of the spring decreases, and less steam from the water supply can be passed on to the ventilation air. Also, as the humidification chamber is permanently under pressure generated by the spring, steam penetrates into the interior of the hollow fibers even if the ventilation air stream is stagnant. As the humidity is not carried away by the ventilation air, condensation occurs on the inside of the hollow fibers. The result is an obstruction of single hollow fibers or even of all fibers. The resulting increase in flow resistance in the ventilation air tube is hindering for the user, and makes breathing entirely impossible.

SUMMARY OF THE INVENTION

The present invention provides a ventilation air humidifier with a humidifying output which is independent of the pressure inside the hollow fibers and the humidification of the ventilation air can be adjusted to the requirements of the user.

An advantage of the invention is that the pressure exerted on a humidification chamber and therefore the pressure difference decreasing over the outer surface of the vaporization membrane follows the air path pressure in the breathing equipment. With stagnant ventilation air the same pressure occurs on both sides of the vaporization membrane and a penetration of steam from the humidification chamber to the ventilation air chamber is avoided. Only with an inhalation does steam penetrate the separation membrane due to the difference in pressure relative to the humidification chamber which is generated in the ventilation air chamber. The humidification of the ventilation air is therefore the more intense the more ventilation air is required by the user, thus creating a smaller or larger pressure difference in the ventilation air chamber.

An advantageous embodiment of the ventilation air humidifier duct.

If the ventilation air humidifier is installed in the mean pressure part of the breathing equipment, the pressure difference between antechamber and ventilation air chamber generated during the inhalation is increased and with it the humidification output and the efficiency. By adjusting a higher mean pressure a sufficient pressure difference is adjustable even with higher ventilation air requirements.

A further adjustment between the ventilation air pressure and the pressure difference generated above the membrane can be achieved by means of a respective change of the throttle opening.

Accordingly it is an object of the invention to provide a humidifier for a respiration device which comprises an outer housing which has a respiratory air outer housing inlet and a respiratory air outer housing outlet with at least one passage in the outer housing which has a respiratory air passage inlet and a respiratory air passage outlet arranged adjacent the respective inlet and outlet of the outer housing which is at least partially permeable to a vapor and including a pressure wall in the housing arranged around the passage being movable under pressure with water in the space between the pressure wall and the passage which defines an antechamber around the exterior thereof in the outer housing which may be filled with ventilation air and which is separated from the passage inlet by a throttle.

A further object of the invention is to provide a method of ventilating respiratory air which comprises collecting the respiratory air into an outer housing into an antechamber between a flexible wall surrounding at least one respiratory air passage in a manner such that some of the respiratory air moves into an antechamber between a flexible wall surrounding the passage which has an interior filled with water which when vaporized will pass through the one passage and throttling the air between the antechamber and the passage so as to regulate the portion of air passing through the throttle to end the passage and remaining outside in the antechamber for controlling the humidification of the ventilating air which is passed through the inlet.

A further object of the invention is to provide a humidifier which is simple in design, rugged in construction and economical to manufacture.

The various features of novelty which characterize the invention are pointed out with particularity in the claims annexed to and forming a part of this disclosure. For a better understanding of the invention, its operating advantages and specific object attained by its uses, reference is made to the accompanying drawings and descriptive matter in which preferred embodiments of the invention are illustrated. cl BRIEF DESCRIPTION OF THE DRAWINGS The only FIGURE of the drawings is a sectional view of a humidifier for respiratory air constructed in accordance with the invention.

DETAILED DESCRIPTION OF THE DRAWING

Referring to the drawing in particular, the invention embodied therein comprises a humidifier for a respiratory device which comprises an outer housing 1 having a respiratory air outer housing inlet designated by the arrow 2 and a respiratory air outer housing outlet designated by the arrow 21. At least one passage is arranged in the outer housing between the outer housing inlet and the outer housing outlet which has a passage inlet *7a* for the respiratory air and a passage discharge *7b*. The passage 7 in the embodiment shown comprises a plurality of individual fiber tubes which are at least partially permeable to a vapor under pressure such as steam.

In accordance with a further feature of the invention a pressure wall 13 is arranged in the outer housing 1 and surrounds the fiber tube 7 defining the passage for the respiratory air and it includes at least a portion of flexible material which will move inwardly and outwardly in accordance with the pressure on the interior and in an outer chamber 14 formed between the interior of said outer housing 1 and the outer wall 13. The space around the fiber tube 7 is filled with water 5 which becomes subjected to the pressure of the antechamber 14. A feature of the invention is that throttle means in the form of a ventilatable air chamber 17 is defined over the inlet 7*a* and which is formed by a dome shaped wall 8 having a throttle 10 which may be formed by regulating a throttle insert piece 9 so as to control the proportion of air which is circulated through the passages of the fiber tube 7 or directed around into the outer antechamber 14.

The ventilation air humidifier outer housing 1 forms a part of a supply tube or duct for the ventilation air coming from a ventilation air source and delivered to a ventilation air connection piece .with a respirator (not shown). The ventilation air flows in the inhalation direction of the arrow 2. The housing 1 has a bottom 3 to which a humidification chamber 4 containing the water supply 5 for humidification purposes is fastened. The side of the humidification chamber 4 opposite the bottom 3 is closed by means of a face or top plate 6. Several hollow fibers tubes or ducts 7 are surrounded by the water of the water supply 5 and they are embedded in the bottom 3 and the face plate 6. The inlet openings 7*a* of the hollow fibers 7 in the face plate 6 are roofed by a face wall or dome 8 having a throttle section 9 with a throttle opening 10. The face wall 8 forms a dome shaped ventilation air chamber 17. The outlet openings 7*b* of the hollow fibers 7 in the bottom 3 are connected to a continuation section of a ventilation air tube 12 by means of a socket 11. The air flow in the direction of the outlet, flow arrow 21, is continued inside the ventilation air tube, to the ventilation air connection piece and then to the respirator (not shown).

The housing 1 surrounds and is spaced from an outside wall 13 of the humidification chamber 4, so that the antechamber 14 is formed which is connected on one end to the supplied ventilation air. The antechamber 14 is under pressure and is connected on its other end with the inlet openings 7*a* of the hollow fibers 7 in the face plate 6. The face plate 6 has an opening 16 closable by means of a plug 15 through which the water supply 5 can be refilled.

During stagnant flow, i.e. when the user does not breathe, the same pressure prevails in the antechamber 14, the ventilation air chamber 17 and the hollow fibers 7. In this case, ventilation air humidification does not take place because, due to the missing pressure difference, a penetration of steam or vapor from the water supply 5 into the hollow of the fibers 7 is avoided. If, in contrast, the ventilation air flows in the direction of the arrows 2 and 21, a pressure difference prevails between the antechamber 14 and the interior of the hollow fibers 7, so that the pressure exerted on the flexible outside wall 13 of the humidification chamber 4 transports steam from the water supply 5 through the hollow fibers 7 into their interior and humidifies the ventilation air. The pressure difference generatable with one inhalation can be determined by an adjustment of the mean pressure in the ventilation air tube 1 and therefore in the antechamber 14, and also by the respective choice of the throttle opening 10.

What is claimed is:

1. A humidifier for a respiratory device comprising an outer housing having a respiratory air outer housing inlet and a respiratory air outer housing outlet, at least one passage having a respiratory air passage inlet and a respiratory air passage outlet arranged in said outer housing with said passage outlet in a flow stream from said outer housing inlet, a pressure wall in said outer housing, at least a portion of said wall being made of flexible material which is movable in response to pressure changes of said wall, water between said at least one passage and said pressure wall, said pressure wall being spaced inwardly from the interior of said outer housing and thereby defining an antechamber between said pressure wall and the interior of said outer housing, said antechamber being in communication with said passage inlet, and throttle means between said outer housing inlet, said passage inlet, and said antechamber.

2. An air humidifier according to claim 1, wherein said at least one passage comprises a bundle of hollow fiber tubes.

3. A humidifier according to claim 2, including a face plate at one end of said passage and a bottom at the other end of said passage, said at least one passage comprising a plurality of hollow fiber tubes having respective ends embedded in said face plate and said bottom, said throttle means comprising a wall overlying said face plate between said passage inlet and said outer housing inlet.

4. A humidifier according to claim 3, in combination with a respiratory device, said device having a respiratory air duct, said outer housing being connected in said duct.

5. A humidifier according to claim 1, wherein said throttle means includes an adjustable throttle member.

6. A method of humidifying respiratory air comprising the steps of (1) providing a humidifier, in combination with a breathing device having an air duct, said humidifier having an outer housing that has an inlet and an outlet, said humidifier further having an antechamber, a flexible wall, at least one respiratory air passage having an inlet and an outlet, and throttle means;

said antechamber being formed between said wall and the interior of said outer housing;

said outer housing outlet being connected in said breathing device air duct;

(2) providing water between said at least one passage and said wall;

(3) drawing respiratory air into the outer housing and antechamber through the outer housing inlet;

(4) throttling the respiratory gas that is drawn through said outer housing inlet into said antechamber, between said antechamber and said respiratory air passage inlet, into said at least one respiratory air passage, so as to regulate the amount of air passed into said respiratory air passage;

(5) humidifying the respiratory air while it passes through said respiratory air passage;

(6) allowing the humidified respiratory air to exit said at least one respiratory air passage via said respiratory air passage outlet into said outer housing outlet, and exit said outer housing outlet via said breathing device air duct; and (7) supplying the humidified respiratory air to a patient via said breathing device air duct.

7. A method of humidifying respiratory air according to claim 6, further including the steps of (1) forming said at least one respiratory air passage by (a) providing a bundle of hollow fiber tubes, a face plate at one end of said flexible wall between said throttle means and said respiratory air passage inlet, and a bottom plate at the other end of said flexible wall between said respiratory air passage outlet and said outer housing outlet;

(b) embedding and aligning said bundles of hollow fiber tubes in said face and bottom plates;

(c) said at least one respiratory air passage communicating respiratory air between said outer housing and respiratory passage inlets and said respiratory passage and outer housing outlets.

8. A method of humidifying respiratory air according to claim 7, further including the steps of (1) forming a dome-shaped wall over said faceplate and said at least one respiratory air passage inlet;

(2) forming said dome shaped wall with a hole that comprises said throttle means; and (3) aligning said throttle means with said outer housing inlet.

* * * * *